US011235003B2

(12) United States Patent
Ankersmit

(10) Patent No.: US 11,235,003 B2
(45) Date of Patent: Feb. 1, 2022

(54) PHARMACEUTICAL PREPARATION COMPRISING SUPERNATANT OF BLOOD MONONUCLEAR CELL CULTURE

(75) Inventor: Hendrik Jan Ankersmit, Vienna (AT)

(73) Assignee: APOSCIENCE AG, Vienna (AT)

( * ) Notice: Subject to any disclaimer, the term of this patent is extended or adjusted under 35 U.S.C. 154(b) by 591 days.

(21) Appl. No.: 13/140,097

(22) PCT Filed: Dec. 18, 2009

(86) PCT No.: PCT/EP2009/067534
§ 371 (c)(1),
(2), (4) Date: Nov. 3, 2011

(87) PCT Pub. No.: WO2010/079086
PCT Pub. Date: Jul. 15, 2010

(65) Prior Publication Data
US 2012/0045418 A1    Feb. 23, 2012

(30) Foreign Application Priority Data
Dec. 18, 2008  (EP) ..................... 08450198

(51) Int. Cl.
*A61K 35/14* (2015.01)
*A61K 35/17* (2015.01)
*A61K 35/16* (2015.01)

(52) U.S. Cl.
CPC .............. *A61K 35/14* (2013.01); *A61K 35/16* (2013.01); *A61K 35/17* (2013.01)

(58) Field of Classification Search
CPC ......... A61K 35/14; A61K 35/16; A61K 35/17
USPC ....................................................... 435/408
See application file for complete search history.

(56) References Cited

U.S. PATENT DOCUMENTS

| 6,399,372 | B1 * | 6/2002 | Bartholeyns | ......... | C12N 5/0645 |
| | | | | | 435/325 |
| 7,118,746 | B1 * | 10/2006 | Naughton | ................ | A23L 1/30 |
| | | | | | 424/184.1 |
| 2006/0004189 | A1 * | 1/2006 | Gandy | .......................... | 530/399 |
| 2011/0177015 | A1 * | 7/2011 | Friedlander | ............ | A61K 8/983 |
| | | | | | 424/70.1 |

FOREIGN PATENT DOCUMENTS

WO    WO 2005/065269 A2 *  7/2005

OTHER PUBLICATIONS

Dent et al. (Stress and Radiation-induced Activation of Multiple Intracellular Signaling Pathways. Radiation Research 159, 283-300; 2003).*
Kitigawa et al. (Activation of Extracellular Signal-regulated Kinase by Ultraviolet Is Mediated through Src-dependent Epidermal Growth Factor Receptor Phosphorylation. Journal of Biological Chemistry. vol. 277, No. 1, Issue of Jan. 4, pp. 366-371, 2002).*
Haneda et al. (Transforming Growth Factorβ Secreted from CD4 T Cells Ameliorates Antigen-Induced Eosinophilic Inflammation. Am. J. Respir. Cell Mol. Biol. 1999).*
Ankersmit et al. (Irradiated cultured apoptotic peripheral blood mononuclear cells regenerate infarcted myocardium. European Journal of Clinical Investigation. 2009 vol. 39, pp. 445-456).*
Beer et al. (Analysis of the Secretome of Apoptotic Peripheral Blood Mononuclear Cells: Impact of Released Proteins and Exosomes for Tissue Regeneration, Nature Scientific Reports. 2015 5:16662, pp. 1-18).*
Hatzi et al. (Expression of receptors for human angiogenin in vascular smooth muscle cells. 1999 Eur. J. Biochem. 260, 825-832).*
Simader et al. (Safety and tolerability of topically administered autologous, apoptotic PBMC secretome (APOSEC) in dermal wounds: a randomized Phase 1 trial (MARSYAS I). 2017 Nature Scientific Reports 7: 6216 pp. 1-8).*
Trojan et al. (Expression of pro-angiogenic growth factors VEGF, EGF and bFGF and their topographical relation to neovascularisation in prostate cancer. Urol Res. May 2004;32(2):97-103).*
Simader et al. (Tissue-regenerative potential of the secretome of γ-irradiated peripheral blood mononuclear cells is mediated via TNFRSF1B-induced necroptosis. Simader et al. Cell Death and Disease (2019) 10:729).*
Werner et al. (Regulation of Wound Healing by Growth Factors and Cytokines. Physiol Rev 83: 835-870 2003).*
Pinto et al. (An Evaluation of the Spontaneous Proliferation of Peripheral Blood Mononuclear Cells in HTLV-1-Infected Individuals Using Flow Cytometry. ISRN Oncology vol. 2011, Article ID 326719, 6 pages).*
Lijnen et al. In vitro proliferative response of human peripheral blood mononuclear cells to concanavalin A. Clinica Chimica Acta 264 (1997) 91-101).*
Katial et al. (Cytokine Production in Cell Culture by Peripheral Blood Mononuclear Cells from Immunocompetent Hosts. Clinical and Diagnostic Laboratory Immunology. Jan. 1998, p. 78-81 vol. 5, No. 1).*
Deenadayalan et al. (Comparison of whole blood and PBMC assays for T-cell functional analysis, BMC Research Notes 2013, 6: 120).*
Arbor Assays (Oxidative Stress as a Result of Acute Hypoxia. 2017, pp. 1-4).*
Olsson, S., et al., "Low Concentrations of Cytokines Produced by Allergen-stimulated Peripheral Blood Mononuclear Cells Have Potent Effects on Nasal Polyp-derived Fibroblasts", Clinical and Experimental Immunology, vol. 132, No. 2, May 2003, pp. 254-260.

(Continued)

*Primary Examiner* — Sharmila G Landau
*Assistant Examiner* — Natalie M Moss
(74) *Attorney, Agent, or Firm* — Workman Nydegger

(57) ABSTRACT

The present invention relates to a topical pharmaceutical preparation for treating an inflammatory skin condition, preferably a condition associated with ischemia, comprising a supernatant of a physiological solution obtainable by cultivating peripheral blood mononuclear cells (PBMCs) or a subset thereof in a physiological solution free of PBMC-proliferating and PBMC-activating substances for at least 1 h.

15 Claims, 20 Drawing Sheets

(56) References Cited

OTHER PUBLICATIONS

Rosloniec, Jr., E. F., et al., "Induction of T-cell Proliferation and Enhancement of NK Activity by Supernatants from Con A-stimulated Human Peripheral Blood Mononuclear Cells: A New Lymphokine", Cellular Immunology, Academic Press, vol. 99, No. 1, Apr. 15, 1986, pp. 170-181.
EP 08450198.0 Search Report dated May 8, 2009.
PCT/EP2009/067534 Written Opinion of the International Searching Authority dated Jun. 11, 2010.
Haslik, W., et al., "Management of full-thickness skin defects in the hand and wrist region: first long-term experiences with the dermal matrix Matriderm", J Plast Reconstr Aesthet Surg (2008) doi: 10.1016/j bjps 2008.09.26.
Friedlander, Hymie; U.S. Appl. No. 61/102,843, filed Oct. 5, 2008 (related to cited art; downloaded from Patentscope).
Sigma-Aldrich PBMC; *Human PBMC Isolation and Counting Using the Scepter™ 2.0 Handheld Automated Cell Counter*; https://www.sigmaaldrich.com/technical-documents/articles/biology/human-pbmc-isolation-and-counting-using-scepter-cell-counter.html (accessed Mar. 21, 2020).

\* cited by examiner

CD31

UC LL

40x

100x

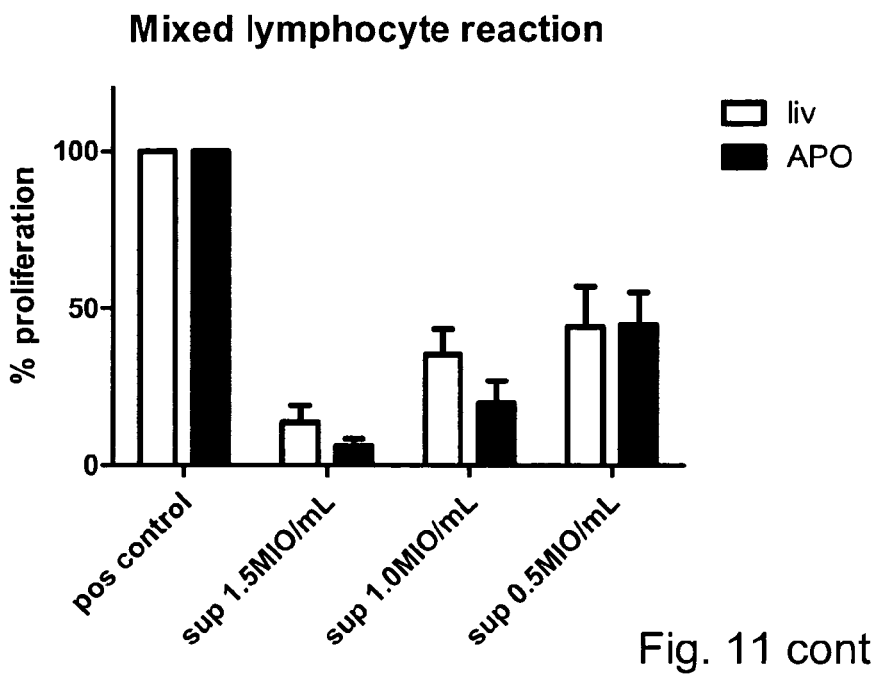
Fig. 11 cont.
Fig. 12
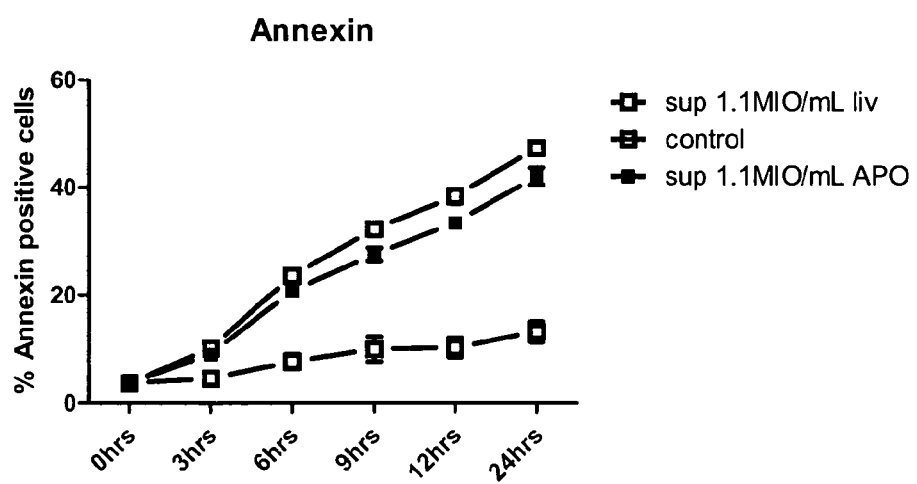

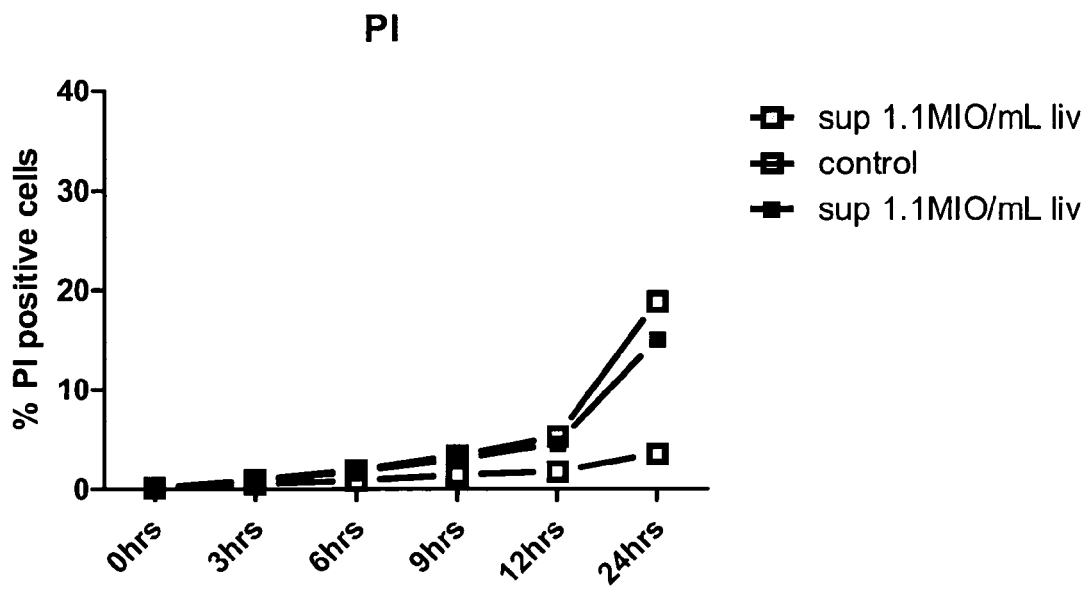
Fig. 12 cont.
Fig. 13
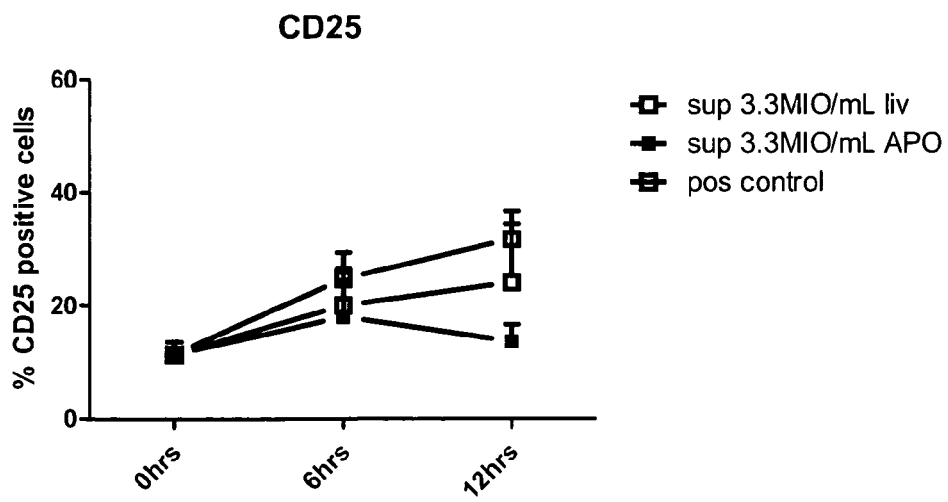

PHARMACEUTICAL PREPARATION COMPRISING SUPERNATANT OF BLOOD MONONUCLEAR CELL CULTURE

This application is a national phase application of PCT/EP2009/067534, filed Dec. 18, 2009, which claims priority to European Patent Application No. 08450198.0 filed Dec. 18, 2008, the disclosures of which are incorporated herein by reference in their entirety.

The present invention relates to a pharmaceutical preparation for treating internal inflammatory skin condition, preferably internal skin conditions associated with ischemia.

Hypoxia, a state of reduced oxygen, can occur when the lungs are compromised or blood flow is reduced. Ischemia, reduction in blood flow, can be caused by the obstruction of an artery or vein by a blood clot (thrombus) or by any foreign circulating matter (embolus) or by a vascular disorder such as atherosclerosis. Reduction in blood flow can have a sudden onset and short duration (acute ischemia) or can have a slow onset with long duration or frequent recurrence (chronic ischemia). Acute ischemia is often associated with regional, irreversible tissue necrosis (an infarct), whereas chronic ischemia is usually associated with transient hypoxic tissue injury. If the decrease in perfusion is prolonged or severe, however, chronic ischemia can also be associated with an infarct. Infarctions commonly occur in the spleen, kidney, lungs, brain and heart, producing disorders such as intestinal infarction, pulmonary infarction, ischemic stroke and myocardial infarction.

Pathologic changes in ischemic disorders depend on the duration and severity of ischemia, and on the length of patient survival. Necrosis can be seen within the infarct in the first 24 h and an acute inflammatory response develops in the viable tissue adjacent to the infarct with leukocytes migrating into the area of dead tissue. Over succeeding days, there is a gradual breakdown and removal of cells within the infarct by phagocytosis and replacement with a collagenous or glial scar.

Hypoperfusion or infarction in one organ often affects other organs. For example, ischemia of the lung, caused by, for example, a pulmonary embolism, not only affects the lung, but also puts the heart and other organs, such as the brain, under hypoxic stress. Myocardial infarction, which often involves coronary artery blockage due to thrombosis, arterial wall vasospasms, or viral infection of the heart, can lead to congestive heart failure and systemic hypotension. Secondary complications such as global ischemic encephalopathy can develop if the cardiac arrest is prolonged with continued hypoperfusion. Cerebral ischemia, most commonly caused by vascular occlusion due to atherosclerosis, can range in severity from transient ischemic attacks (TIAs) to cerebral infarction or stroke. While the symptoms of TIAs are temporary and reversible, TIAs tend to recur and are often followed by a stroke.

Occlusive arterial disease includes coronary artery disease, which can lead to myocardial infarction, and peripheral arterial disease, which can affect the abdominal aorta, its major branches, and arteries of the legs. Peripheral arterial disease includes Buerger's disease, Raynaud's disease, and acrocyanosis. Although peripheral arterial disease is commonly caused by atherosclerosis, other major causes include, e.g., diabetes, etc. Complications associated with peripheral arterial disease include severe leg cramps, angina, abnormal heart rhythms, heart failure, heart attack, stroke and kidney failure.

Ischemic and hypoxic disorders are a major cause of morbidity and mortality. Cardiovascular diseases are responsible for 30% of deaths worldwide. Among the various cardiovascular diseases, ischemic heart disease and cerebrovascular diseases cause approximately 17% of deaths.

Currently, treatment of ischemic and hypoxic disorders is focused on relief of symptoms and treatment of causative disorders. For example, treatments for myocardial infarction include nitroglycerin and analgesics to control pain and relieve the workload of the heart. Other medications, including digoxin, diuretics, amrinone, beta-blockers, lipid-lowering agents and angiotensin-converting enzyme inhibitors, are used to stabilize the condition, but none of these therapies directly address the tissue damage produced by the ischemia and hypoxia.

Due to deficiencies in current treatments, there remains a need for methods that are effective in treating conditions involving hypoxia. There is also a need for methods that are effective in the prevention of tissue damage caused by ischemia that occurs due to, e.g., atherosclerosis, diabetes and pulmonary disorders.

Conditions associated with ischemia and hypoxia are usually accompanied by inflammation. Therefore means and methods are needed which also reduce inflammation.

It is an object of the present invention to provide means which allow the efficient treatment of inflammatory conditions, preferably conditions associated with ischemia.

The present invention relates to a topical pharmaceutical preparation for treating an inflammatory skin condition, preferably a skin condition associated with ischemia, comprising a supernatant of a physiological solution obtainable by cultivating peripheral blood mononuclear cells (PBMCs) or a subset thereof in a physiological solution free of PBMC-proliferating and PBMC-activating substances for at least 1 h.

It turned out that the administration of a pharmaceutical preparation as defined above to a patient suffering from an inflammatory skin condition, preferably a skin condition associated with ischemia, results in an alleviation of the respective symptoms and in a healing process.

The pharmaceutical preparation of the present invention comprises the supernatant of cultivated PBMCs or a subset thereof. In the course of the cultivation of PBMCs these cells express and secrete substances like cytokines which differ from those expressed and secreted in activated PBMCs. This means that the secretome of PBMCs of the present invention is different from the secretome of activated PBMCs. The cells of the present invention undergo a non-cell-surface moiety triggered secretome production. Therefore it is surprising that the supernatant of PBMCs which have not been contacted with PBMC activating substances like PHA or LPS can be employed to treat inflammatory skin conditions, which shows that the secretome of these cells comprises substances supporting the treatment of said conditions. The supernatant is particularly suited to treat ischemic skin condition.

The PBMC supernatant according to the present invention is obtainable by cultivating them in a physiological solution which does not comprise PBMC-proliferating and PBMC-activating substances. However, the PBMCs are incubated in the physiological solution for at least 1 h. This minimum time of cultivation is required to let the PBMCs secrete cytokines and other beneficial substances.

PBMCs part of the preparation according to the present invention can be obtained from whole blood using methods known in the art such as ficoll gradient, hypotonic lysis etc. These methods are well known in the art.

PBMCs of the pharmaceutical preparation may be obtained from a pool of donors or from the same individual to which the preparation will be administered.

The physiologic solution from which the supernatant is obtained comprises at least 500, preferably at least 1000, more preferably at least 10', even more preferably at least 10', cells per ml solution or per dosage unit.

"Physiological solution", as used herein, refers to a liquid solution in which PBMCs are cultivated prior their use in the pharmaceutical preparation according to the present invention.

"Physiological solution" refers also to a solution which does not lead to the death of PBMCs within an hour, preferably within 30 min. If the number of viable PBMCs is decreasing in a solution by 75%, more preferably by 90% within one hour, preferably within 30 min, the solution is not considered to be a "physiological solution" as defined herein. The "physiological solution" does not lead to a spontaneous lysis of PBMCs when contacted with said solution.

In this context the step of "cultivating" or "culturing" comprises or consists of the step of "incubating", a step in which the cells are contacted with a solution for a defined time (at least 1 h, preferably at least 4 h, more preferably at least 8 h, even more preferably at least 12 h) under conditions which are regularly used for cultivating PBMCs.

The term "skin condition associated with ischemia" in the context of the present invention can be used interchangeable with the term "ischemic skin conditions" and denotes any condition, disease or disorder in which regions of the human or animal body are deprived of adequate oxygen supply resultant damage or dysfunction of tissue. A pathological condition may be characterized by reduction or abolition of blood supply within the skin or part thereof, which may be caused by the constriction or obstruction of a blood vessel. Such conditions are collectively referred to herein by the term "ischemia" or "ischemia related skin conditions" or "skin condition related to ischemia". In heart disease, for instance, ischemia is often used to describe the heart muscle that is not getting the proper amount of oxygen-rich blood because of narrowed or blocked coronary arteries. The symptoms of ischemia depend on the organ that is "ischemic". With the heart, ischemia often results in angina pectoris. In the brain, ischemia can result in a stroke. Ischemia conditions are accompanied by inflammation.

Non-limiting examples for pathological skin conditions which relate to inflammation, in particular to ischemia, include wounds, chronic wounds, diabetic wounds, skin ulcer, psoriasis etc.

Notwithstanding the above, a pathological condition in the context of the invention may be characterized by damage or dysfunction of endothelial cells, i.e. wound. Non-limiting examples of wounds which may be treated by the use of the preparation according to the present invention are chronic wounds, diabetic wounds, ulcer, burns, inflammatory skin disease and bowel disease.

"Physiological solution", as used herein, is preferably a solution exhibiting an osmotic pressure which does not lead to the destruction of the PBMCs or subsets thereof and can be directly administered to an individual.

The term "free of PBMC-proliferating and PBMC-activating substances" refers to the physiological solution which does not comprise substances which activate PBMCs and induce the proliferation of PBMCs or subsets thereof. These substances include PHA, LPS etc.

According to a preferred embodiment of the present invention the inflammatory skin disease is selected from the group consisting of inflammation, hypoxia induced inflammation and autoimmune disease, preferably psoriasis, acne, rosacea, pyoderma gangrenosum, dermatitis, atopic skin disease, contact dermatitis, seborrheic dermatitis, erythema nodosum, infections skin disease caused by bacterial, viral, fungal, parasitic infestations, stings, bites, and urticaria, and skin conditions associated with ischemia. Particularly preferred skin conditions are skin conditions associated with ischemia.

According to a particularly preferred embodiment of the present invention the skin condition associated with ischemia is selected from the group consisting of wounds, tissue ischemia, chronic wounds, diabetic wounds, skin ulcer, skin burns, skin flaps in plastic surgery and tissue regeneration after dental grafting.

The subset of peripheral blood mononuclear cells (PBMCs) is preferably T cells, B cells or NK cells. Of course it is also possible to use combinations of these cells: T cells and B cells; T cells and NK cells; B cells and NK cells; T cells, B cells and NK cells. Methods for providing and isolating said cells are known.

It surprisingly turned out that the PBMCs of the present invention can be cultivated in any kind of solution provided that said solution does not comprise substances which are not pharmaceutically acceptable, lead to an immediate death of the PBMCs (as defined above), activate PBMCs and stimulate the proliferation of PBMCs. Therefore the solution to be used at least exhibits osmotic properties which do not lead to lysis of the PBMCs. The physiological solution is preferably a physiological salt solution, preferably a physiological NaCl solution, whole blood, a blood fraction, preferably serum, or a cell culture medium.

The cell culture medium is preferably selected from the group consisting of RPMI, DMEM, X-vivo and Ultraculture.

According to a particularly preferred embodiment of the present invention the cells of the present invention are cultivated under stress inducing conditions.

The term "under stress inducing conditions", as used herein, refers to cultivation conditions leading to stressed cells. Conditions causing stress to cells include among others heat, chemicals, radiation, hypoxia, osmotic pressure etc.

Additional stress to the cells of the present invention leads to a further increase of the expression and secretion of substances beneficial for treating inflammatory skin conditions, in particular skin conditions associated with ischemia.

According to a preferred embodiment of the present invention the stress inducing conditions include hypoxia, ozone, heat (e.g. more than 2° C., preferably more than 5° C., more preferably more than 10° C., higher than the optimal cultivation temperature of PBMCs, i.e. 37° C.), radiation (e.g. UV radiation, gamma radiation), chemicals, osmotic pressure (i.e. osmotic conditions which are elevated at least 10% in comparison to osmotic conditions regularly occurring in a body fluid, in particular in blood) or combinations thereof.

If radiation is used to stress the PBMCs of the present invention the cells are preferably irradiated with at least 10 Gy, preferably at least 20 Gy, more preferably at least 40 Gy, whereby as source Cs-137 Caesium is preferably used.

According to a preferred embodiment of the present invention the non-activated PBMCs or a subset thereof are cultivated in a medium for at least 4 h, preferably for at least 6 h, more preferably for at least 12 h.

The pharmaceutical preparation according to the present invention is topically administered. Therefore said preparation is preferably provided as a gel, preferably hydrogel, as an ointment, as a dermal patch, as a pharmaceutically acceptable matrix, preferably on a collagen/elastin matrix (see e.g. Haslik W et al. J Plast Reconst Aesth Surg (2008): "*Management of full-thickness skin defects in the hand and wrist region: first long-term experiences with the dermal matrix Matriderm*"), as a paste, as a cream, as a powder, as a liniment or as a lotion.

A pharmaceutical preparation according to the present invention may comprise pharmaceutically acceptable excipients such as diluents, stabilizers, carriers etc. Depending on the dosage form the preparation according to the present invention comprises the respective ingredients. Methods for preparing the same are well known to the skilled artisan.

In order to increase the shelf-life of the preparation according to the present invention the solution a) or the supernatant b) is lyophilised. Methods for lyophilising such preparations are well known to the person skilled in the art.

Prior its use the lyophilised preparation can be contacted with water or an aqueous solution comprising buffers, stabilizers, salts etc.

Another aspect of the present invention relates to the use of a preparation as defined above for the manufacture of a medicament for treating an inflammatory skin condition, in particular a skin condition associated with ischemia.

Yet another aspect of the present invention relates to a method for preparing a topical pharmaceutical preparation as disclosed herein comprising the steps of a) providing peripheral blood mononuclear cells (PBMCs) or a subset thereof, b) culturing the cells of step a) in a physiological solution free of PBMC-proliferating and PBMC-activating substances for at least 1 h, c) isolating the supernatant of step b), and d) preparing the pharmaceutical preparation using the supernatant of step c).

The preparation according to the present invention can be obtained by incubating or culturing PBMCs in a physiological solution for at least 1 h, preferably at least 4 b, more preferably at least 8 h, even more preferably at least 12 h. In the course of this step the PMDCs begin to synthesize and to secrete substances which are useful in the treatment of inflammatory conditions. Prior, after and in the course of the culturing step the cells are not activated by adding PBMC activating substances like PHA or LPS. After the cultivation step the cells and/or the supernatant of the culture is isolated to be further used in the preparation of the final pharmaceutical preparation. As discussed above the pharmaceutical preparation may comprise cultivated PBMCs, the supernatant of the culture in which said cells had been incubated or both the cultivated PBMCs as well as the culture medium.

According to a preferred embodiment of the present invention the cells are subjected to stress inducing conditions before or in the course of step b), wherein said stress inducing conditions include hypoxia, ozone, heat, radiation, chemicals, osmotic pressure (e.g. induced by the addition of salt, in particular NaCl, in order to give an osmotic pressure higher than in blood), pH shift (i.e. pH change by adding acids or hydroxides to give a pH value of 6.5 to 7.2 or 7.5 to 8.0) or combinations thereof.

According to a preferred embodiment of the present invention the cells are irradiated before or in the course of step h) with at least 10 Gy, preferably at least 20 Gy, more preferably at least 40 Gy, with ozone, with elevated temperature or with UV radiation.

Another aspect of the present invention relates to a preparation obtainable by a method as described above.

Another aspect of the present invention relates to a method for treating inflammatory skin conditions, in particular skin conditions associated with ischemia by administering to an individual in need thereof an appropriate amount of the pharmaceutical preparation according to the present invention.

The present invention is further illustrated by the following figures and examples, however, without being restricted thereto.

FIG. 1 shows the effect of peripheral blood mononuclear cell (PBMC)-derived culture supernatants (SN) on cell migration in human primary keratinocytes (KC) and dermal fibroblasts (FB).

KC and FB were grown in KC-growth medium and DMEM (supplemented with 10% FBS), respectively. After reaching confluency the cell monolayer was scratched with a pipette-tip and further cultivated with PBMC-derived SN for 16 h. We could only detect little effect of SN from living PBMCs (LL) on KC, whereas SN from apoptotic PBMCs (APO) strongly induced KC-migration. In contrast both SN (LL and APO) strongly induced cell migration in dermal FB.

FIG. 2 shows the effect of PBMC-derived SN on the cell cycle progression of KC and FB.

Proliferating KC and FB were cultivated in PMBC-derived SN. After 24 h cells were incubated with BrdU for 2 h and further treated as indicated in the user manual (BrdU-FACS flow cell cycle kit, BD Biosciences). As shown in FIG. 2, stimulation of FB with PMBC-derived SN led to a decrease of the proliferating cell population accompanied by an increase of cells in the G2/M phase. In contrast, a significant increase of proliferating KC with both LL- and APO-SN was found. However, the effect of SN derived from apoptotic cells was more pronounced in KC.

FIG. 3 shows PBMC-derived SN strongly enhance wound-healing in vivo.

Creams containing either LL (FIG. 3*a, b*) or APO (FIG. 3*b*) PBMC-SN were applied on 6 mm punch biopsy wounds on the backs of B6/129 mice immediately after wounding. 8 days after wounding the mice were sacrificed and the wounds were analyzed by H&E-staining. As shown in FIGS. 3*a* and 3*b* both SN strongly enhanced wound healing in both the dermal and epidermal compartments of the skin.

FIG. 4 shows PBMC-derived SN strongly enhance wound-healing in vivo.

The wound-size during the first 5 days after wounding until a crust was formed was measured. As shown in FIG. 4 it was found that wound-closure after treatment with creams containing PBMC-derived supernatants was much faster compared to the cream alone during the whole 5 days. Whereas the wound-size increased somewhat during the first 2 days with cream alone, wounds treated with PBMC-derived supernatants began to close during the first 24 h after wounding and application of the creams.

FIG. 5 shows increased angiogenesis in mouse wounds in vivo after treatment with PBMC-derived SN.

By immuno-histochemistry for factor VIII (FIG. 5*a*) and CD31 (FIG. 5*b*), both markers for blood-vessels, a massive increase in CD31 positive cells in SN treated wounds compared to controls, indicative of increased angiogenesis, which could contribute to the enhanced wound-healing, was found. In contrast an increased number of proliferating cell at this time point as analyzed by Ki67 staining could not be detected (FIG. 5*a*).

FIG. 6*a* shows that neither unstimulated viable PBMC or IA-PBMC secrete the mainly monocyte derived pro-inflammatory cytokine TNF-α. (Significances are indicated as follows: * p=0.05, ** p=0.001; n=8)

FIG. 6b demonstrates a strong induction of pro-inflammatory Interferon-γ secretion after activation as compared to unstimulated PBMC. (Significances are indicated as follows: * p=0.05, ** p=0.001; n=8)

FIG. 7a shows pooled results of flow cytometric analysis. PBMCs were gated for T cells and expression of activation markers CD69 and CD25 were evaluated. (Significances are indicated as follows: * p=0.05, ** p=0.001; n=4)

FIG. 7b displays a representative FACS analysis of PBMCs either activated (PHA, CD3 mAb). Gating represents % of positive cells.

FIG. 12 shows the level of Annexin V and PI positivity of the supernatant of CD4+ cells inoculated with PBMC supernatants.

EXAMPLES

Example 1

Figure 1:
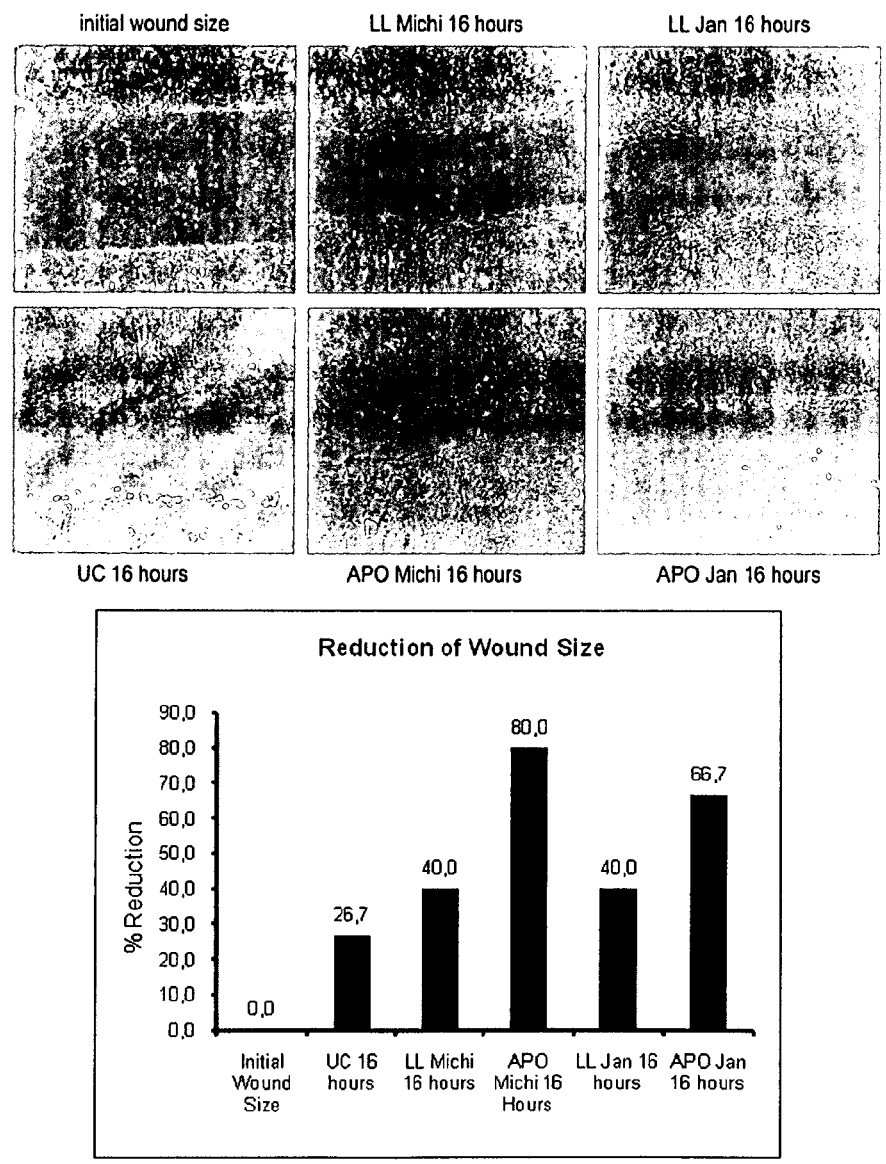
Figure 1:
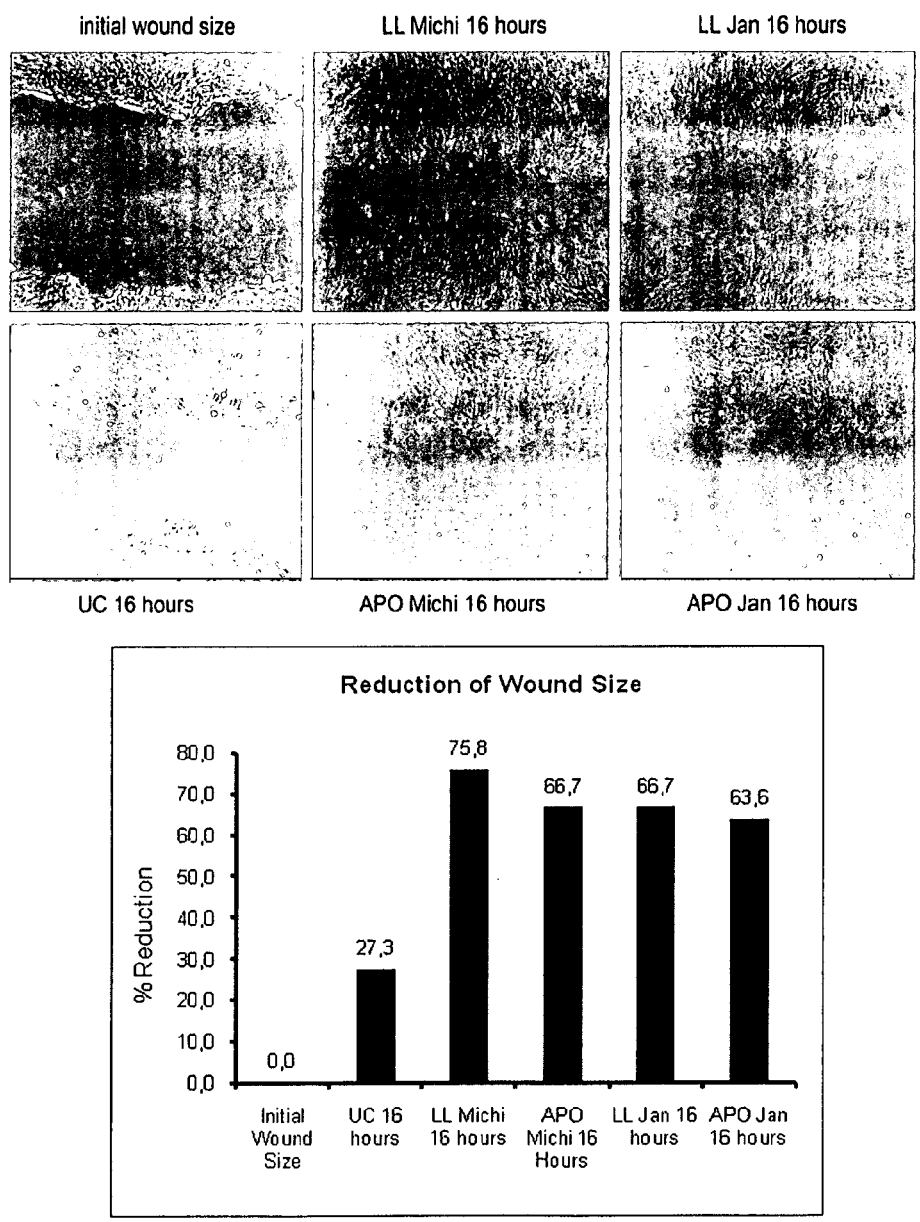
Figure 2:
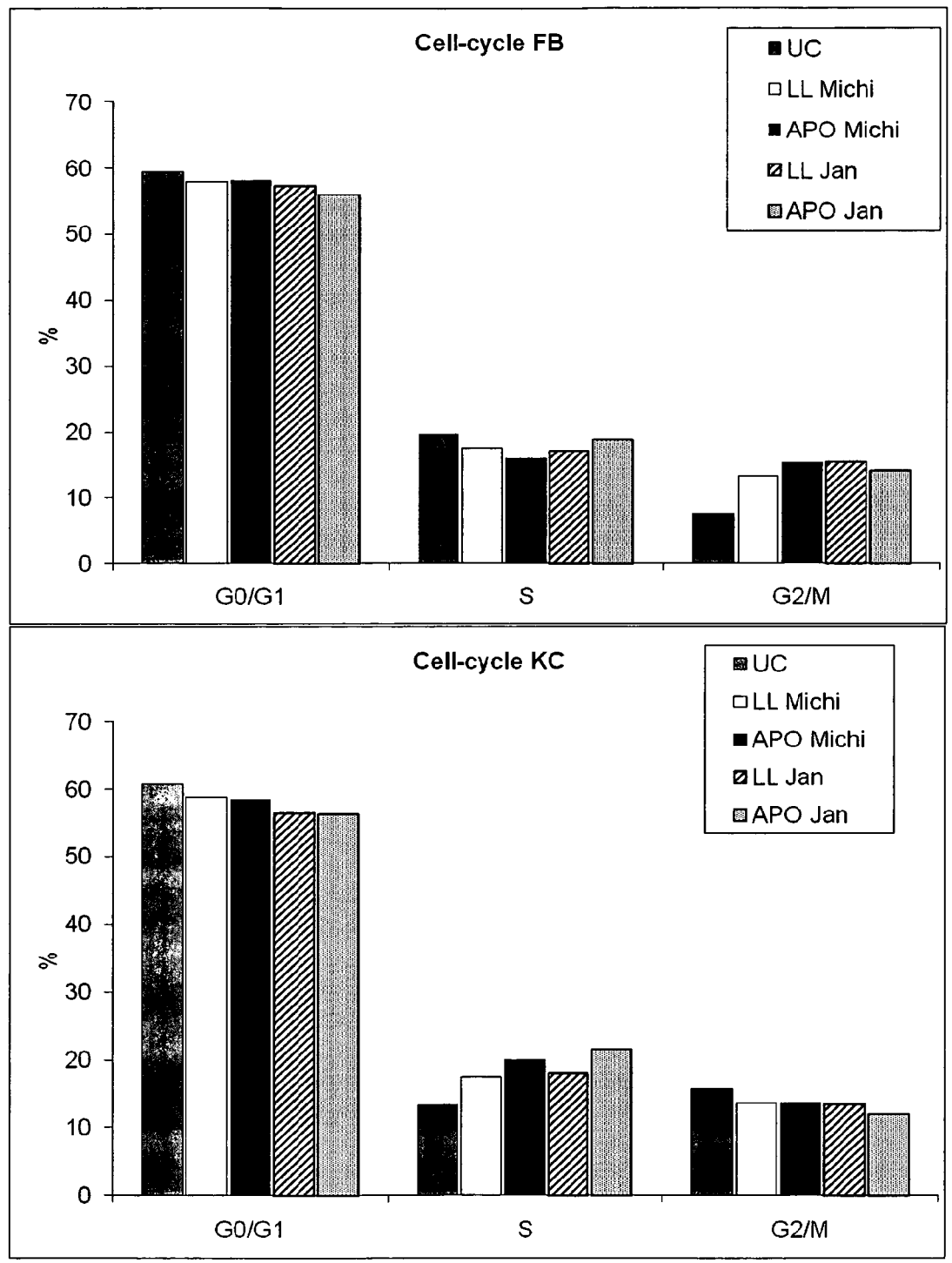
Figure 3A:
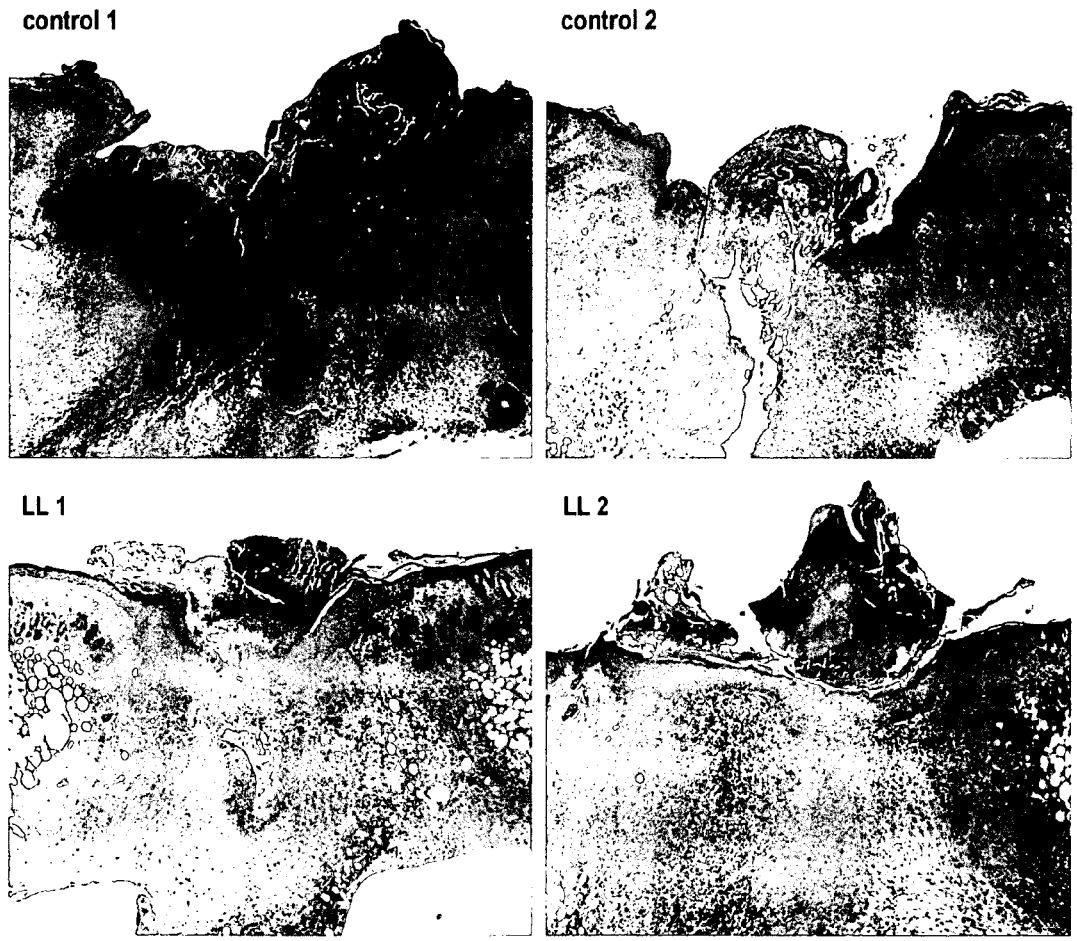
Figure 3B:
Figure 4:
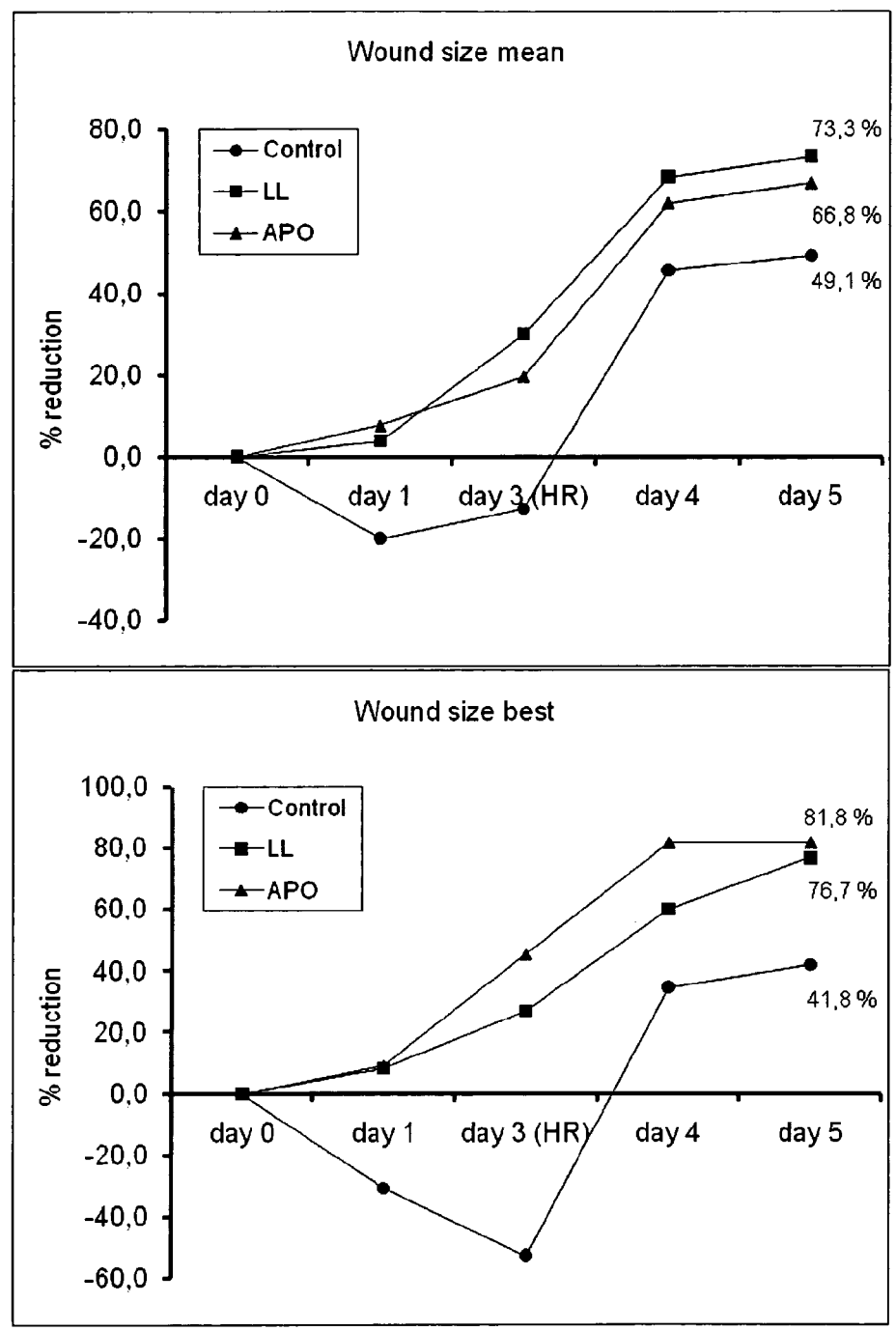
Figure 5A:
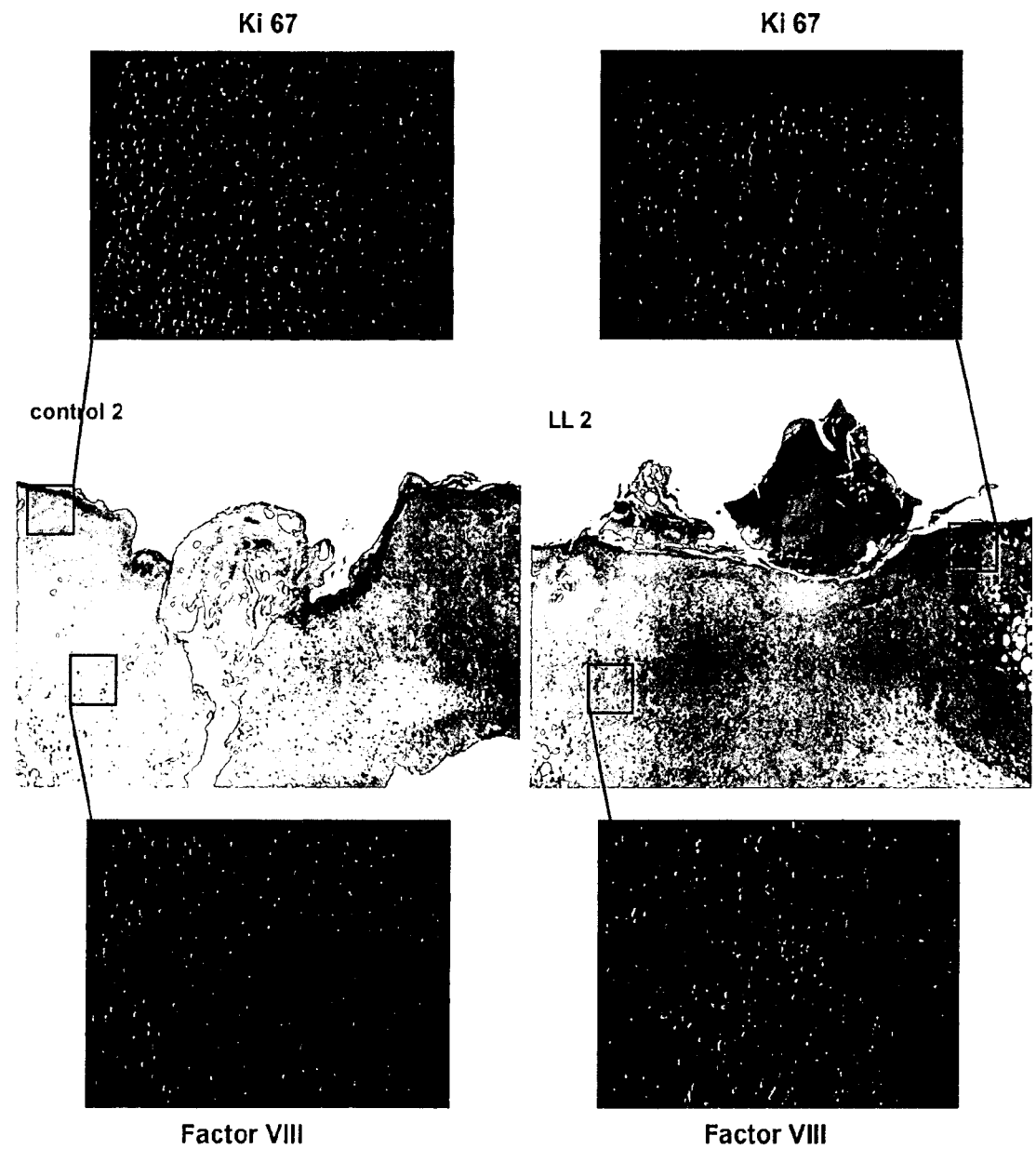
Figure 5B:
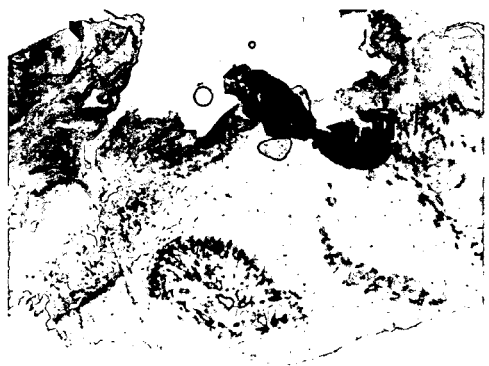
Figure 5B:
Figure 5B:
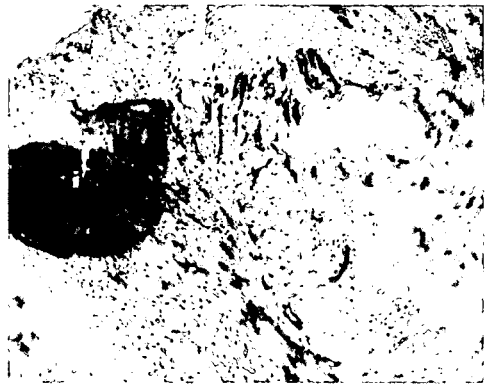
Figure 5B:
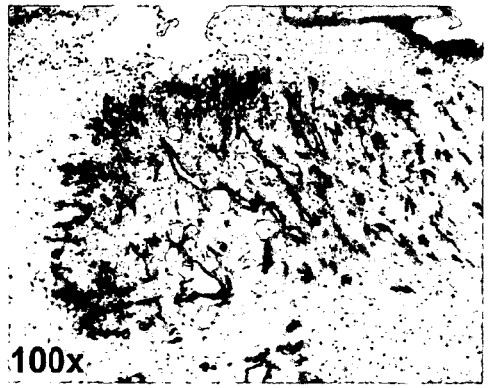

Culture Supernatants of Peripheral Blood Mononuclear Cells Strongly Enhance Wound Healing Non-healing skin ulcers are often resistant to most common treatments. In a previous study it was shown that application of peripheral blood mononuclear cells (PBMCs) together with basic fibroblast growth factor appeared to be a useful treatment for diabetic gangrene. In the present example it was investigated whether culture supernatants of PBMCs (either non-irradiated or irradiated) are sufficient to induce enhanced wound healing in a mouse model. Furthermore the effect of these supernatants on human primary fibroblasts (FB), keratinocytes (KC) and endothelial cells (EC) was analyzed.

By incubation of FE and KC with PBMC-derived supernatants it was found that supernatants of both non-irradiated and irradiated cells strongly induced migration of FB, whereas they had no effect on FB-proliferation. By contrast, it was shown that both supernatants were effective on KC with respect to their migration- and proliferation capacity. However the effect of supernatants derived from irradiated cells was more pronounced. Since PBMC-derived supernatants induced the migratory and proliferatory machinery in vitro, it was further investigated whether these supernatants are also able to induce wound-healing in vivo. Therefore PBMC-supernatant containing creams were prepared and applied on 6 mm punch biopsy wounds on the backs of B6/129 mice immediately after wounding. The wound-size was measured during the next 4-5 days until a crust was formed. It was surprisingly found that wound-closure after treatment with creams containing PBMC-derived supernatants was much faster compared to the cream alone during the whole 5 days. Interestingly, whereas the wound-size increased somewhat during the first 2 days with cream alone, wounds treated with PBMC-derived supernatants began to close during the first 24 h after wounding and application of the creams. 8-10 days after wounding the mice were sacrificed and the wounds were analyzed by H&E-staining and by immuno-histochemistry for CD31, a marker for blood-vessels. H&E staining revealed that wound healing in both the dermal and epidermal compartments of the skin was more advanced in the presence of creams from PBMC-derived supernatants. Furthermore there was a massive increase in CD31 positive cells in such wounds, indicative of increased angiogenesis, which could contribute to the enhanced wound-healing.

In summary it was shown that PBMC-derived supernatants led to enhanced wound-healing in mice in vivo and that these supernatants also induced proliferation and migration in human cells in vitro. The formulation of creams containing PBMC-supernatants might represent a big advantage for the treatment of non-healing skin ulcers (see FIG. 1 to 5).

Example 2

Resting Peripheral Blood Mononuclear Cells (PBMC) Evidence Low Activation Marker and Reduced Inflammatory Cytokine Production Activated peripheral blood mononuclear cells (PBMCs) and their supernatants (SN) are supposed to be beneficial in wound regeneration (Holzinger C et al. Eur J Vasc Surg. 1994 May; 8(3): 351-6). In examples 1 and 2 it could be shown that non-activated PBMC and SN derived thereof has beneficial effects in an experimental acute myocardical infarct (AMI) and wounding model. Since non-activation of PBMC had to be verified experimentally it was investigated whether cultivation of PBMC leads to enhanced T-cell activation markers (CD69, CD25) or enhanced inflammatory cytokine secretion (monocyte activation=TNFα, T-cell activation=INFγ). In a control experiment cultured T cells were triggered by CD3 mAb stimulation or Phytohemagglutinin (PHA).

Methods and Results

Venous blood was collected in EDTA-tubes from healthy volunteers. After Ficoll-Hypaque density grade separation, PBMC were collected and divided into viable and irradiated apoptotic cells (IA-PBMC). To obtain apoptotic cells, PBMC were irradiated with 60 Gy (Caesium-137). For flow cytometric analysis 500,000 PBMC were cultivated in 200 μl serum-free medium. Cells were either stimulated with PHA (7 μg/mL) or CD3-mAb (10 μg/mL) or were left unstimulated. After 24 h of incubation cells were washed, stained for CD3, CD69 and CD25 (R&D System) and evaluated for surface activation markers on a FC500 (Coulter). For ELISA assays PBMC were cultivated overnight at a density of $2.5 \times 10^6$ cells/ml, either with or without PHA or CD3 stimulation. After 24 h supernatants were harvested and frozen at −20° C. Commercially available ELISA kits for TNF-α (R&D) and INF-γ (Bender) were purchased. In short, MaxiSorp plates were coated with anti-bodies against TNF-α and TNF-γ and stored overnight. After 24 h, plates were washed and samples added in duplicates to each well. After incubation and addition of a detection antibody and Strep-Lavidin-HRP, TMB-substrate was added to each well. After color development, the enzymatic reaction was stopped by addition of sulphic acid. Optical density values were read on a Wallac Victor3 plate reader.

Results:

FACS analysis: CD3 and PHA stimulated T cells showed an upregulation of activation markers CD69 and CD25 after 24 h of incubation. Unstimulated and apoptotic cells expressed only low amounts of CD69 and CD25 (FIG. 6a (representative sample, FIG. 6b, histogram, n=4). Statistical significance is indicated by asterix (xx p<0.001, x p<0.05). ELISA analysis: Whereas neither TNF-α and INF-γ in unstimulated PBMC-derived supernatants were detected, supernatants from PHA or CD3 stimulated PBMC evidenced high values for these cytokines as indicated by ELISA analysis (asterix ** p<0.001, * p<0.05, n=8). The results clearly show a different secretion pattern of inflammatory cytokines in comparison to unstimulated PBMC.

Conclusion:

These data indicate that "unstimulated PBMC" evidence a distinct different phenotype (activation marker, cytokine secretion) as compared to stimulated PBMCs (PHA and CD3 mAb).

Figure 6A:
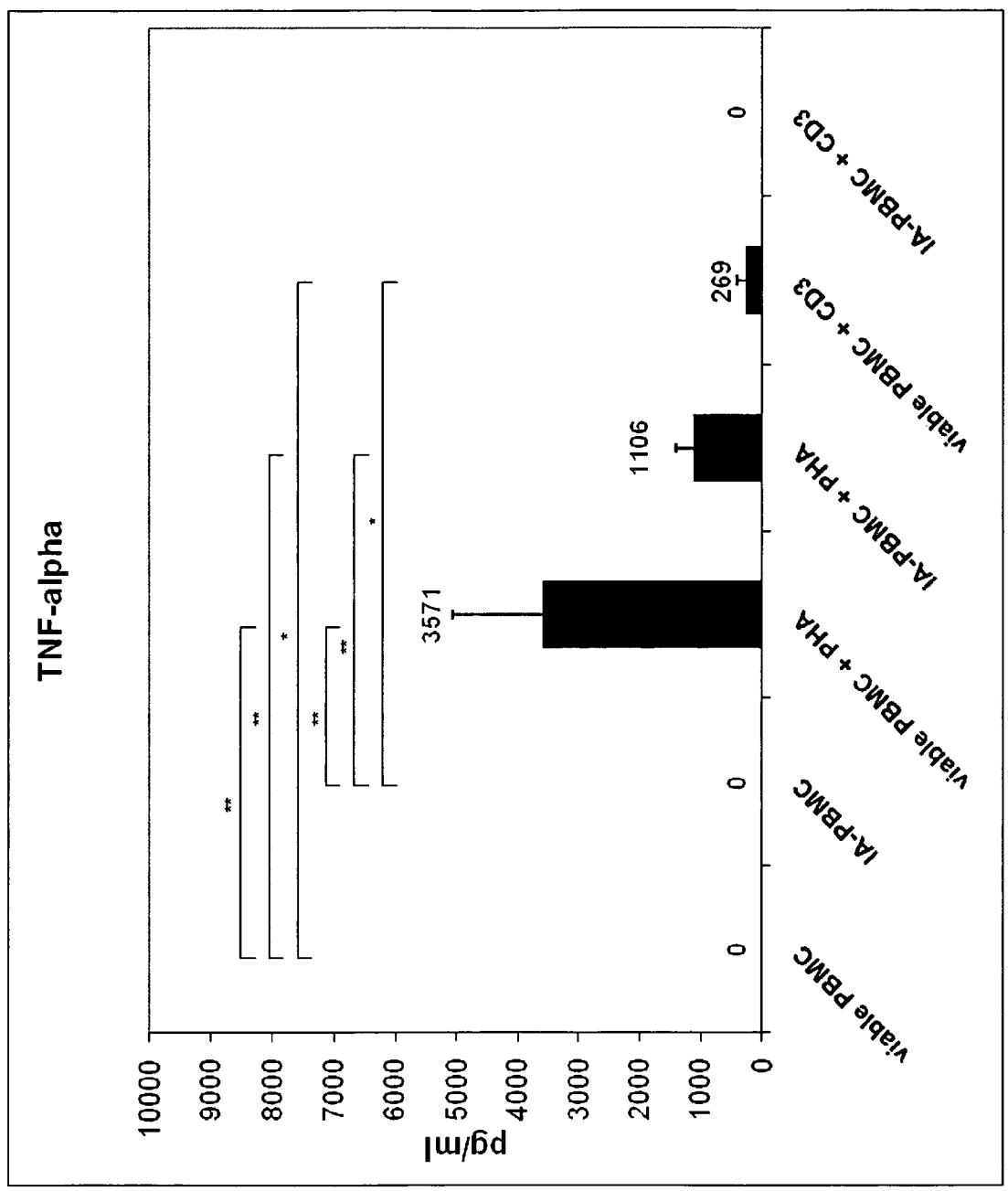

FIG. 6a indicates that neither unstimulated viable PBMC or IA-PBMC secrete the mainly monocyte derived pro-inflammatory cytokine TNF-α. (Significances are indicated as follows: * p=0.05, ** p=0.001; n=8)

Figure 6B:
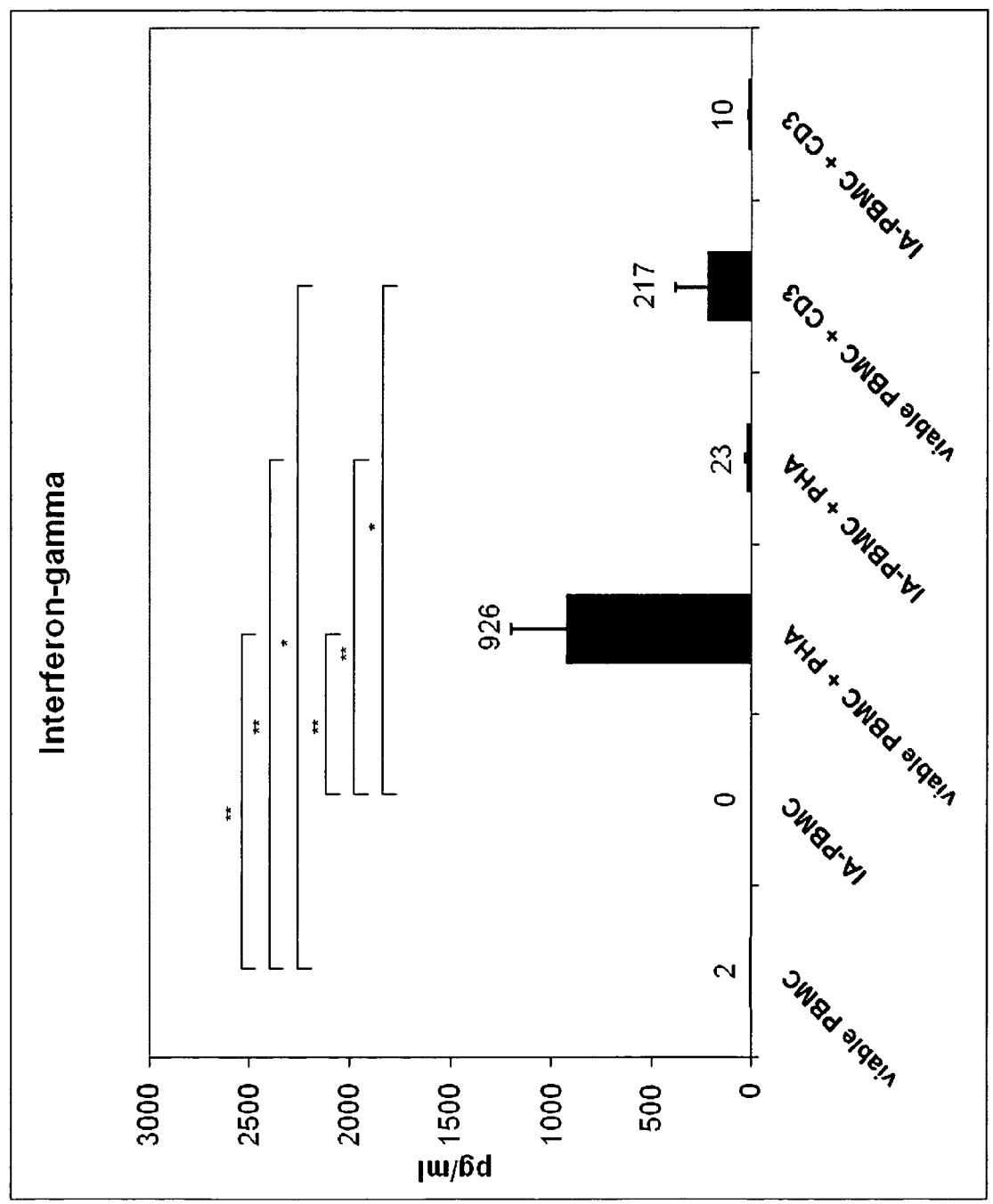

FIG. 6b demonstrates a strong induction of pro-inflammatory Interferon-γ secretion after activation as compared to unstimulated PBMC. (Significances are indicated as follows: * p=0.05, ** p=0.001; n=8)

Figure 7A:
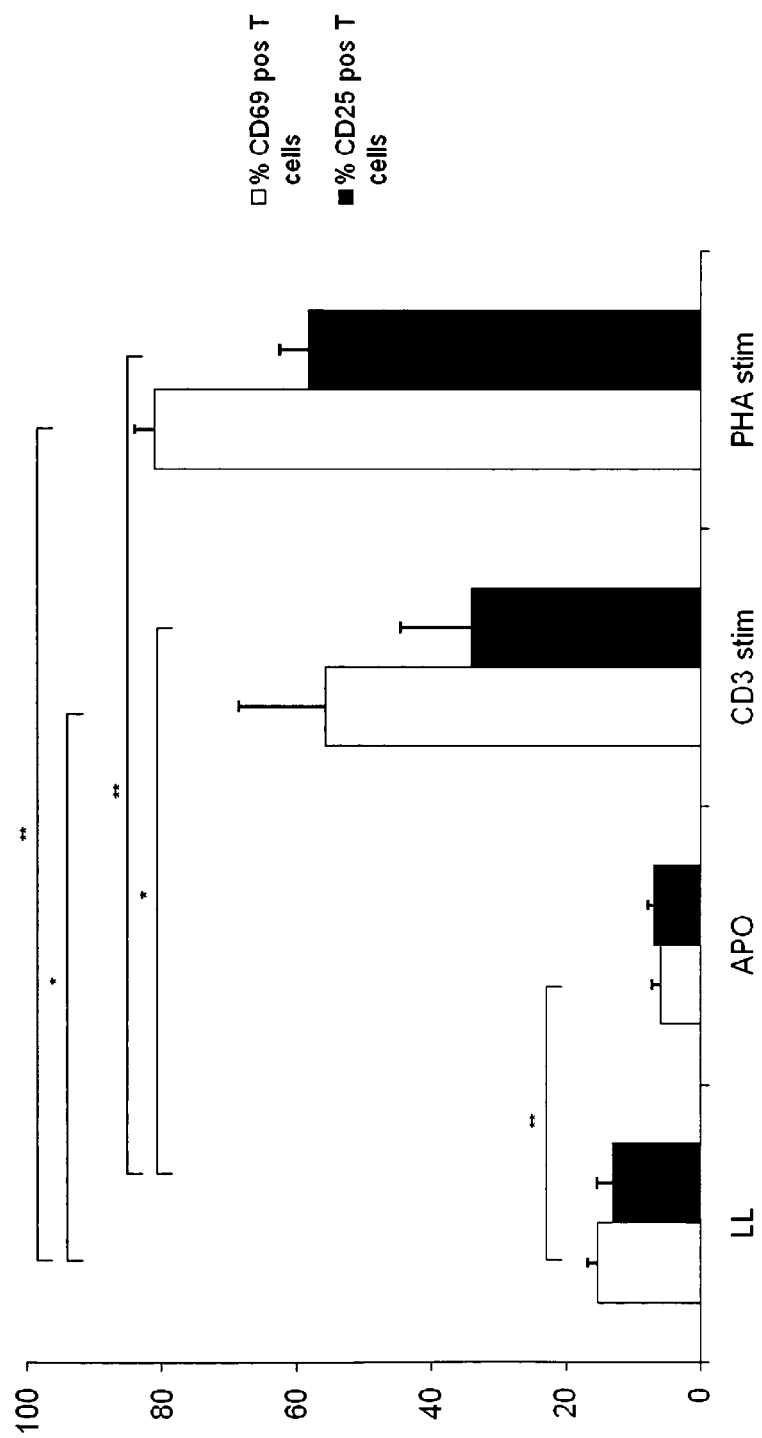

FIG. 7a shows pooled results of flow cytometric analysis. PBMCs were gated for T cells and expression of activation markers CD69 and CD25 were evaluated. (Significances are indicated as follows: * p=0.05, ** p=0.001; n=4)

Figure 7B:
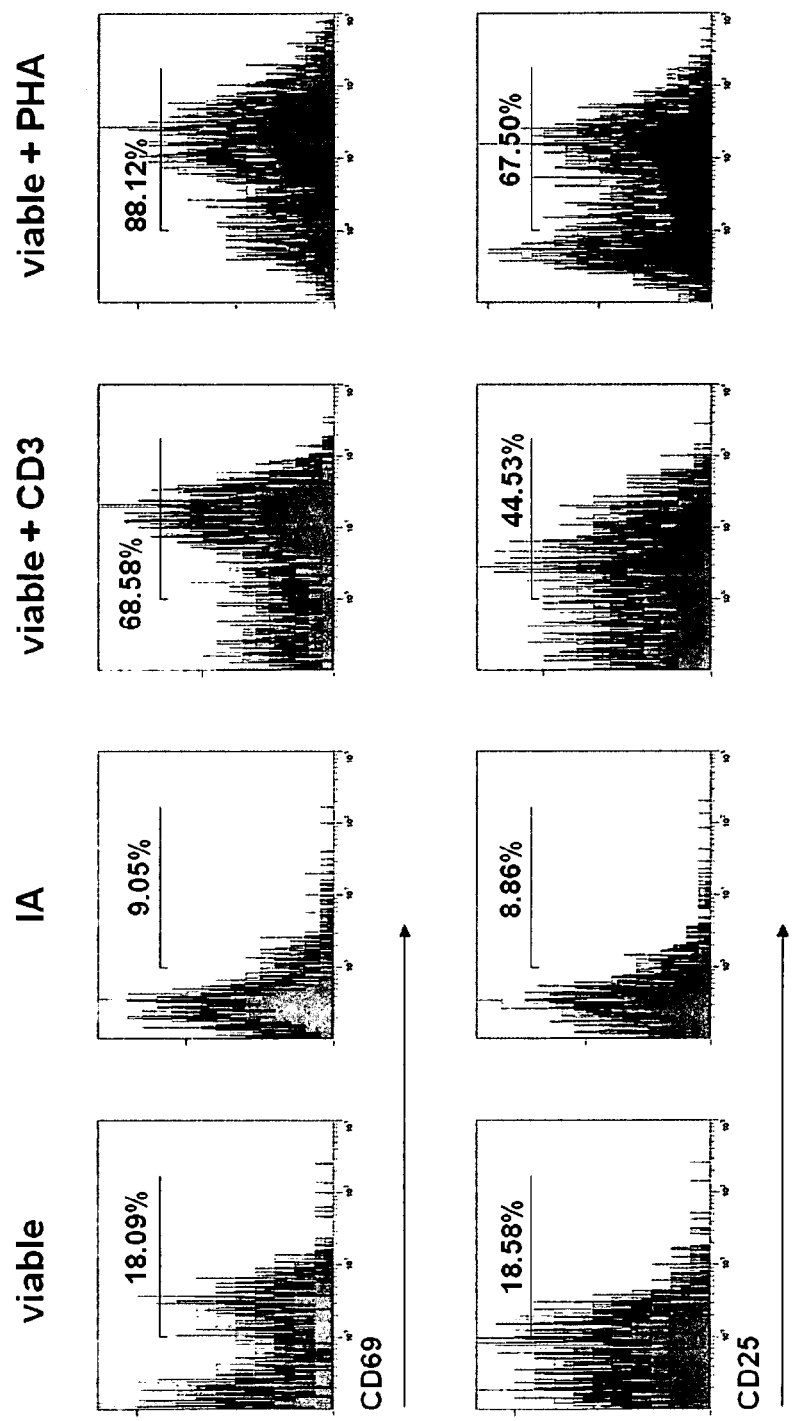

FIG. 7b displays a representative FACS analysis of PBMCs either activated (PHA, CD3 mAb). Gating represents % of positive cells.

Example 3

Proliferative Activity of PBMC Cultivated in a Physiological Solution

The aim of this example is to prove that PBMC have no proliferative activity as compared to immune assays that utilize specific (CD3), unspecific (lectin, PHA) and allogeneic T-cell triggering (mixed lymphocyte reaction, MLR) in a 2 day (CD3, PHA) and 5 day (MLR) stimulation assay.

Material and Methods

PBMC were separated from young healthy volunteers by Ficoll density gradient centrifugation and resuspended in RPMI (Gibco, USA) containing 0.2% gentamycinsulfate (Sigma Chemical Co, USA), 1% L-Glutamin (Sigma, USA) at $1*10^5$ cells per 200 µL. Responder cells were either stimulated by MoAb to CD3 (10 µg/mL, BD, NJ, USA), PHA (7 µL/mL, Sigma Chemical Co, USA) or with irradiated allogeneic PBMC at a 1:1 ratio (for MLR). Plates were incubated for 48 h or 5 days and then pulsed for 18 h with 3[H]-thymidine ($3.7*10^4$ Bq/well; Amersham Pharmacia Biotech, Sweden). Cells were harvested and 3[H]-thymidine incorporation was measured in a liquid scintillation counter.

Figure 8:
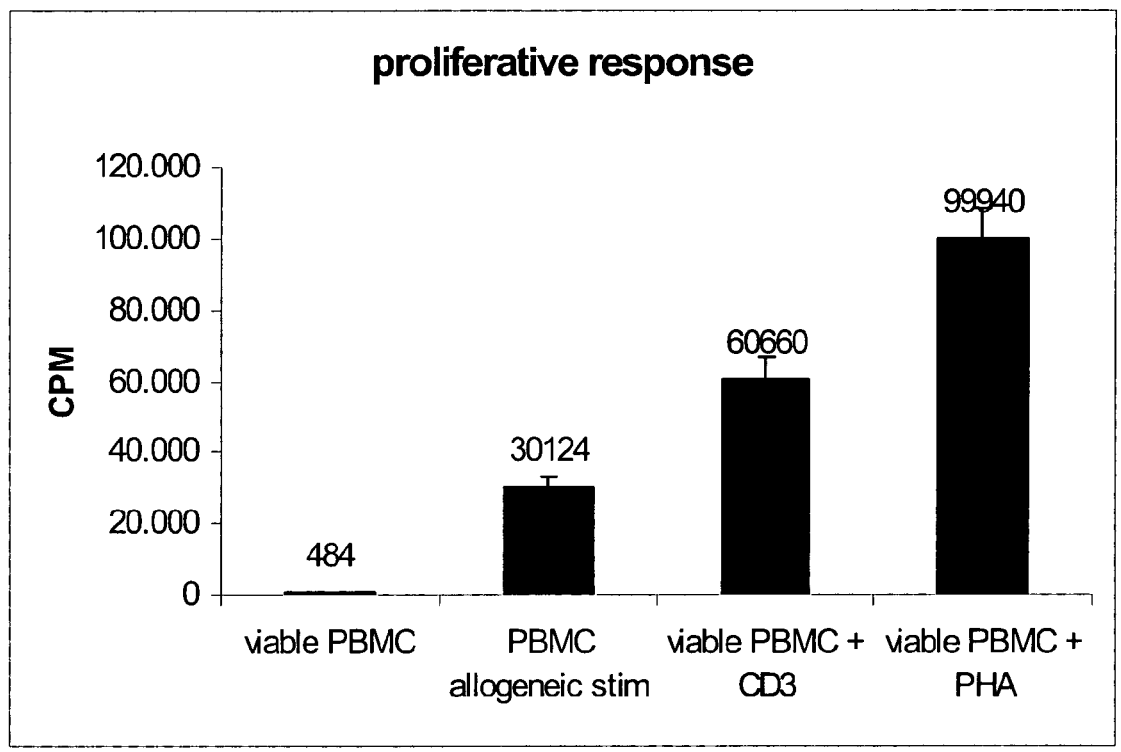
FIG. 8 shows high proliferation rates as measured by 3[H]-thymidine incorporation of stimulated PBMC when compared to viable PBMC cultured in RPMI without stimulation.

Results:

Stimulated PBMC showed high proliferation rates as measured by 3[H]-thymidine incorporation when compared to viable PBMC cultured in RPMI without stimulation (FIG. 8). This effect was observed by adding T cell specific stimuli (PHA, CD3) as well as in assays where proliferation was triggered by antigen presenting cells (MLR).

Conclusion:

This set of experiments implicates that viable PBMC held in culture for up to 5 days do not proliferate whereas PENS stimulated by different ways showed a marked proliferative response. It is concluded that culture of PBMC without stimulation does not lead to proliferative response.

Example 4

Secretoma of Separated PBMC Kept Under Sterile Culture Conditions Possess Neo-Angionetic Capacity Since neo-angionesis and inflammation are strongly linked in vivo it was investigated whether these secretoma of PBMC also exhibit anti-proliferative effects on T cells and therefore interfere with an inflammatory immune response.

Material and Methods

Secretoma were obtained by incubating PBMC ($2.5*10^6$/mL) from young healthy volunteers separated by Ficoll density gradient centrifugation for 24 h in RPMI (Gibco, CA, USA) containing gentamycinsulfate (Sigma Chemical Co, USA), 1% L-Glutamin (Sigma, USA). Supernatants were separated from the cellular fraction and stored at −80° C. For proliferation assays allogeneic PBMC were resuspended at $1*10^5$ cells per 200 µL RPMI after separation. Responder cells were either stimulated by MoAb to CD3 (10 µg/mL, BD, USA) or PHA (7 µL/mL, Sigma Chemical Co, USA). Different dilutions of supernatants were added. Plates were incubated for 48 h and then pulsed for 18 h with $^3$[H]-thymidine ($3.7*10^4$ Bq/well; Amersham Pharmacia Biotech, Sweden). Cells were harvested and $^3$[H]-thymidine incorporation was measured in a liquid scintillation counter.

Figure 9:
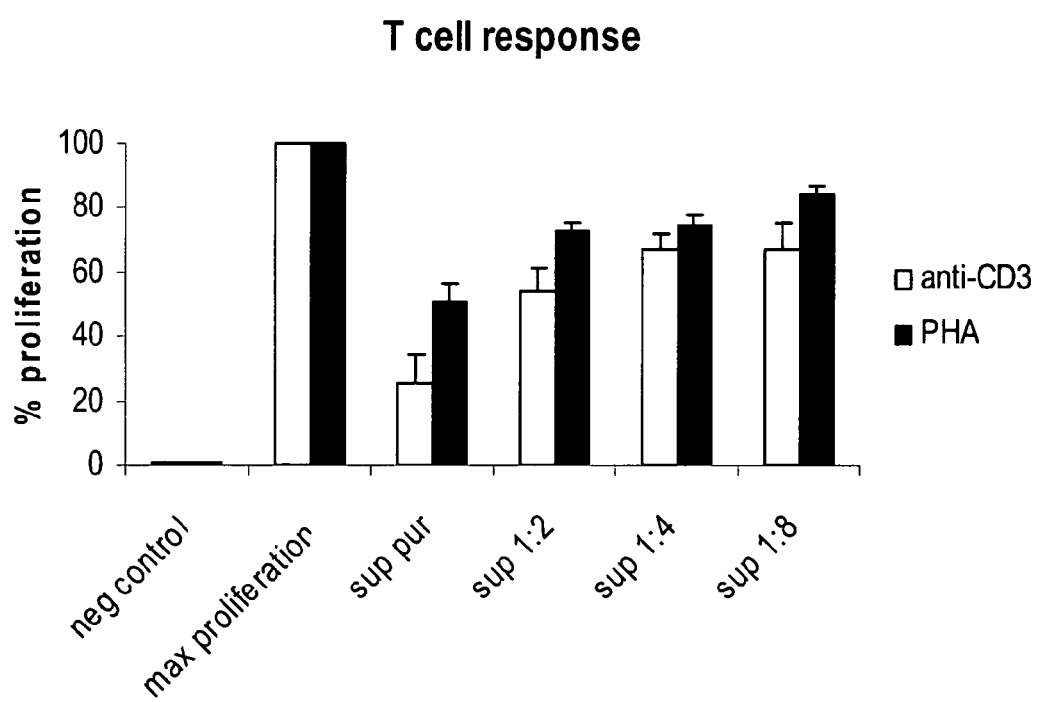
FIG. 9 shows inhibition of T cell response of PBMC secretoma in T cell proliferation assays.

Results:

Secretoma of allogeneic PBMC evidenced a significant reduction of proliferation rates measured by $^3$[H]-thymidine incorporation when compared to positive controls (FIG. 9). This effect was dose-dependent and could be seen upon anti-CD3 as well as upon PHA stimulation.

Implication:

This set of experiments implicates that secretoma obtained from viable PBMC held in culture for 24 h exhibit significant anti-proliferative effects in vitro. These data indicate that supernatant derived from PBMC or in lyophilised form may serve as potential therapeutic formula to treat human diseases that are related to hypoxia induced inflammation or other hyperinflammatory diseases (e.g. autoimmune diseases, inflammatory skin diseases).

Example 5

Paracrine Factors Secreted by Peripheral Blood Mononuclear Cells Posses Immunesuppressive Features In Example 1 anti-inflammatory effects of PBMC secretoma in an acute myocardial infarction (AMI) animal model are evidenced. In this example it is shown that the application of PBMC secretoma after AMI induction inhibits the inflammatory damage of the heart muscle by massively down-regulating the immune response.

Based on these findings possible immunesuppressive effects of secretoma in vitro experiments were investigated. CD4+ cells play a key role in the orchestration of the immune response as they are pivotal for the assistance of other leukocytes (e.g. macrophages, B cells, cytotoxic T cells) in immunological processes.

Material and Methods

Production of PBMC Secretoma

PBMC from healthy volunteers were separated by Ficoll density centrifugation. Cells were resuspended in Ultra Culture Medium (Lonza, Basel, Switzerland) at a concentration of $1*10^6$ cells/mL (sup liv). For the production of secretoma from apoptotic PBMC apoptosis was induced by irradiation with 60 Gy (sup APA). Cells were incubated for 24 h in a humidified athmosphere (5% CO2, 37° C., relative humidity 95%). Supernatants were removed and dialysed with a 3.5 kDa cutoff (Spectrum laboratories, Breda, The Netherlands) against 50 mM ammonium acetate overnight at 4° C. Then supernatants were sterile filtrated and lyophilized. Lyophilized secretoma were stored at −80° C. and freshly resuspended for every experiment. Secretoma were random sampled for their pH value.

Separation of CD4 Cells

CD4+ cells were separated by depletion of non-CD4+ T cells utilizing a MACS bead system (Miltenyi, Bergisch Gladbach, Germany). Cells were freshly prepared and immediately used for each experiment.

Measurement of Apoptosis

Apoptosis was detected by flow cytometry using a commercially available Annexin V/PI kit (BD, New Jersey, USA). Apoptosis were defined by Annexin positive staining, late apoptosis by PI positivity.

Proliferation Experiments

PBMC or purified CD4+ cells were diluted in Ultra Culture supplemented with 0.2% gentamycinsulfate (Sigma, St. Louis, Mo., USA), 0.5% β-mercapto-ethanol (Sigma, St Louis, Mo., USA) and 1% GlutaMAX-I (Invitrogen, Carlsbad, Calif., USA) to a concentration of $1*10^5$/well in a 96 round-bottom well plate. Cells were stimulated with either PHA (7 µg/mL, Sigma, USA), CD3 (10 µg/mL, BD, New Jersey, USA) IL-2 (10 U/mL, BD, USA) or an 1:1 ratio of allogeneic irradiated (60 Gy) PBMC for MLR. Cells were incubated for 48 h or 5 days (MLR) with different concentrations of PBMC secretoma, IL-10 or TGF-β. Then cells were pulsed for 18 h with 3[H]-thymidine ($3.7 \times 10^4$ Bq/well; Amersham Pharmacia Biotech, Uppsala, Sweden). Cells were harvested and 3[H]-thymidine incorporation was measured in a liquid scintillation counter.

Activation Markers

Purified CD4+ cells were stimulated with anti-CD3 (10 µg/mL) and co-incubated with different concentration of PBMC secretoma. Cells were stained for CD69 and CD25 following a standard flow cytometric staining protocol and analyzed on a flow cytometer FC500 (Beckman Coulter, Fullerton, Calif., USA).

Results

In preliminary experiments the anti-proliferative properties of PBMC supernatants from viable cells (sup liv) were tested. In anti-CD3 and PHA stimulation experiments proliferations rates were significantly reduced by the addition of secretoma (n=10).

Figure 10:
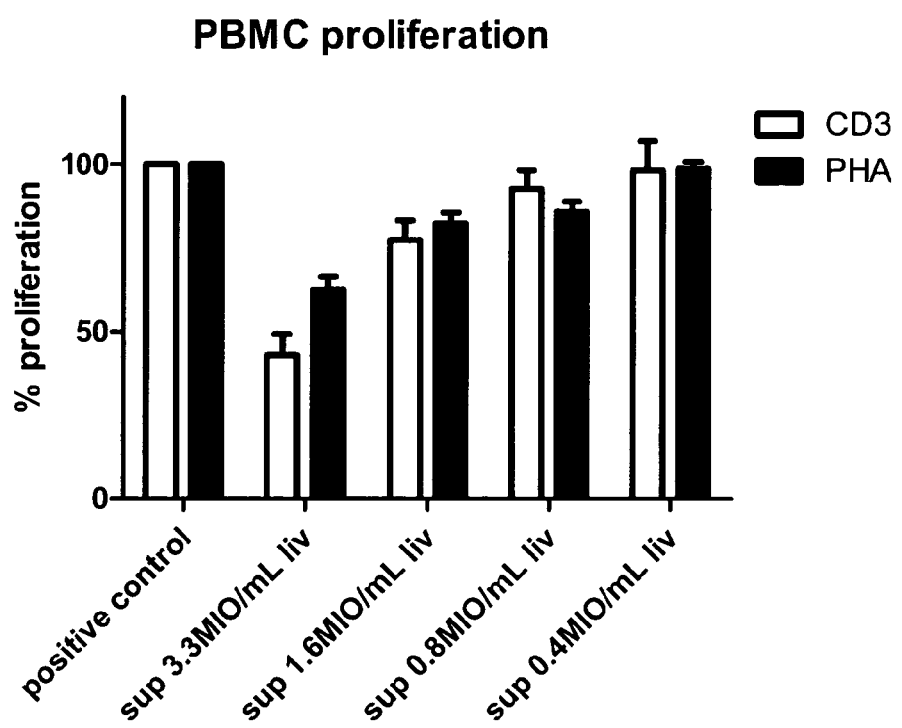
FIG. 10 shows anti-CD3 and PHA stimulation experiments performed with PBMC.
Figure 11:
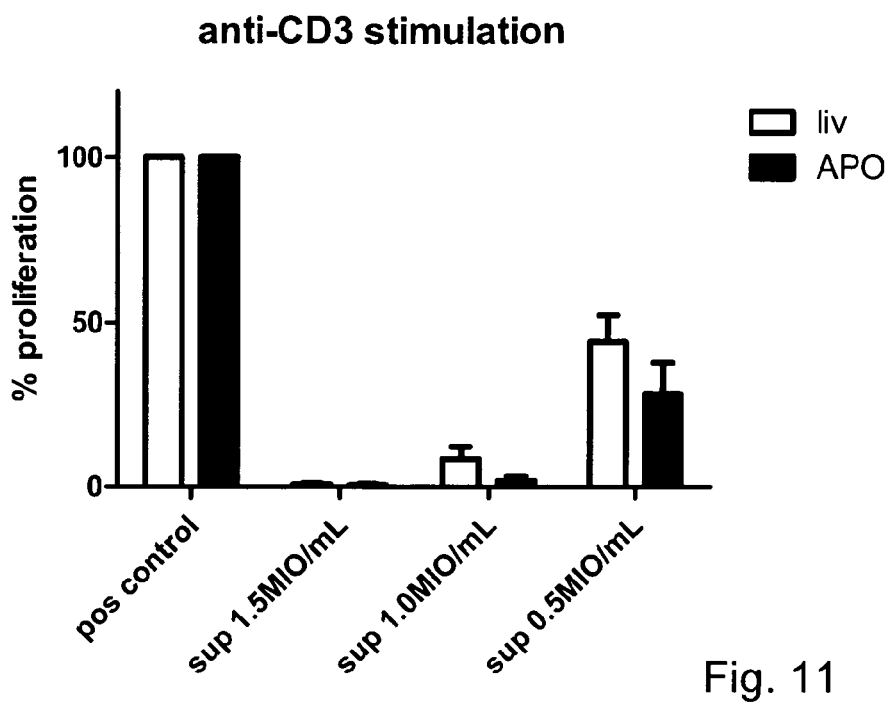
FIG. 11 shows the proliferation of PBMC upon stimulation with anti-CD3, PHA and mixed lymphocytes.
Figure 11:
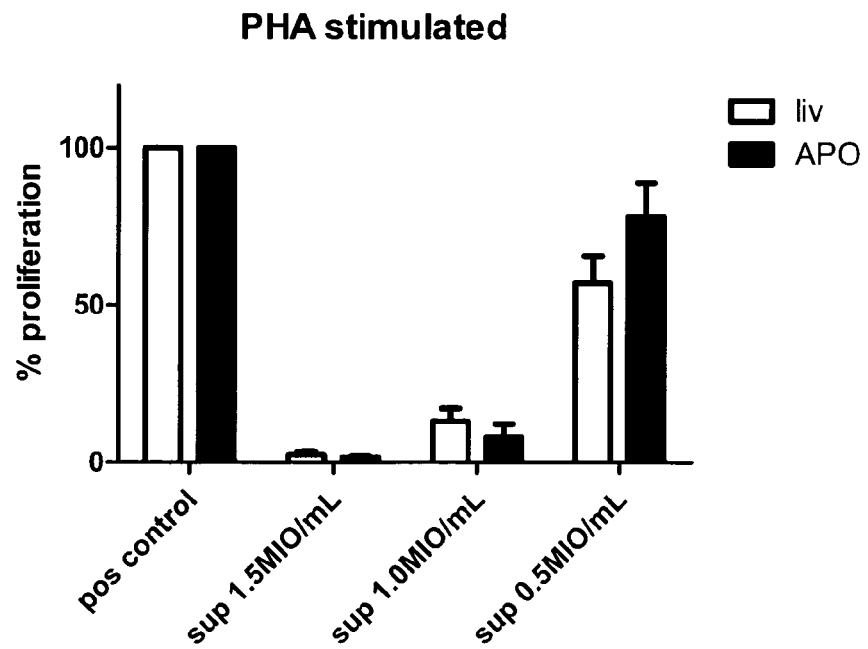

Based on these findings the effect of PBMC secretoma on the T-helper cell compartment was evaluated, since these cells play a pivotal role in launching and perpetuating an immune response. In analogy to FIG. 10 highly purified CD4+ cells lost their proliferative capacity by the addition of secretoma. This phenomenon was observed for the supernatant of living as well as of apoptotic, irradiated PBMC (FIG. 11, n=5).

The next step was to determine possible effects of the secretoma on cell viability. Therefore resting CD4+ cells were inoculated with supernatant and Annexin V and PI positivity was evaluated. Supernatants from both, living and apoptotic PBMC, evidenced remarkable pro-apoptotic effects (FIG. 12, n=5).

Figure 13:
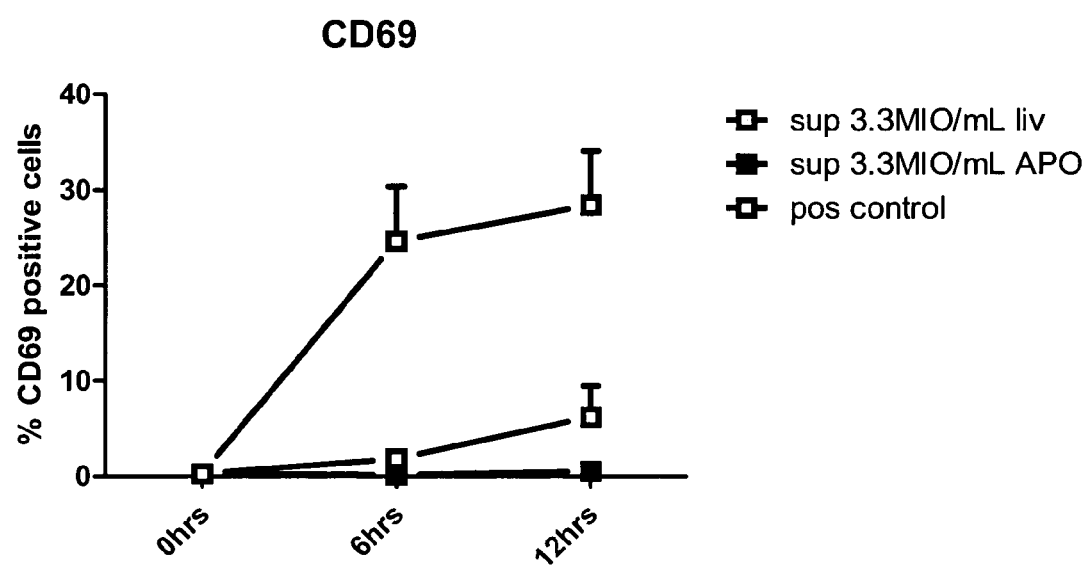
FIG. 13 shows the inhibition of the up-regulation of CD25 and CD69 in CD4+ cells by PBMC supernatant.

To test if PBMC secretoma were able to inhibit CD4+ cell activation the T cell activation markers CD25 and CD69 following anti-CD3 stimulation of CD4+ cells was evaluated. The up-regulation of both markers was significantly and dose-dependent inhibited by PBMC secretoma (FIG. 13, n=5).

Figure 14:
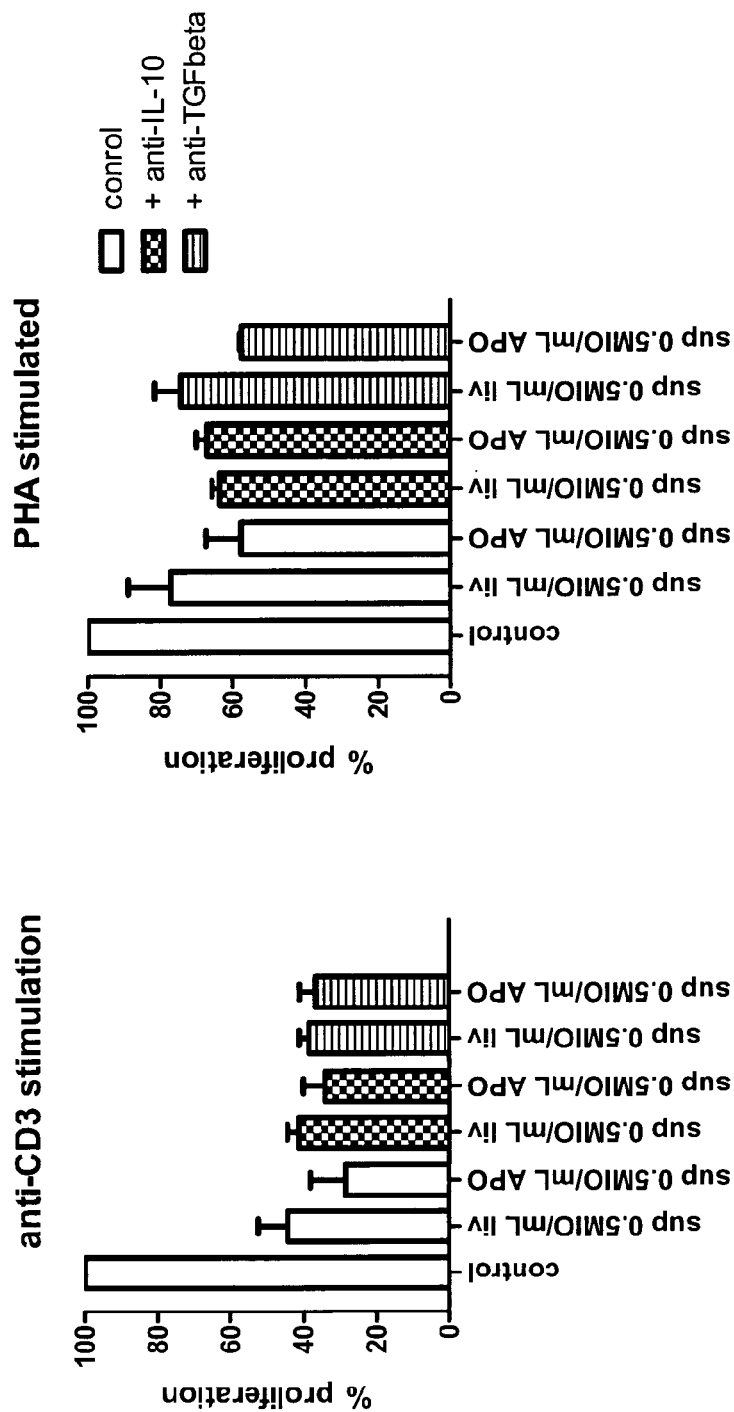
FIG. 14 shows that the demonetizing of IL-10 and TGF-β did not increase she proliferation rates of CD4+ cells.

In a last set of experiments the effect of the immune-suppressive cytokines IL-1C and TGF-β by the addition of neutralizing antibodies in these experiments was examined. Neither IL-10 and TGF-(was found to be responsible for the anti-proliferative effects of our PBMC secretoma, since demonetizing these cytokines did not increase proliferation rates (FIG. 14, n=5).

Conclusion

These experiments evidence for the first time that PBMC secretoma posses immune-suppressive features in vitro. It was shown that supernatant a) reduces proliferation rates in anti-CD3, PHA and MLR stimulation experiments, b) has the potency to induce apoptosis and inhibits activation of CD4+ cells upon T cell triggering.

The invention claimed is:

1. A method of topically treating an ischemia associated inflammatory skin condition by a step of administering a topical pharmaceutical preparation to an affected area,
    wherein the topical pharmaceutical preparation comprises a culture supernatant obtained by in vitro cultivation of peripheral blood mononuclear cells (PBMCs) comprising T cells, B cells, NK cells, and monocytes obtained by Ficoll density gradient centrifugation,
    wherein the PBMCs are cultivated for at least 1 h within a physiological solution that is a culture medium free of phytohemagglutinin (PHA) and lipopolysaccharide (LPS),
    wherein before or during the course of cultivation, the PBMCs are subjected to a stress inducing condition, that includes irradiation with at least 60 Gy, and
    wherein the culture supernatant includes a secretome produced by said PBMCs during in vitro cultivation within said physiological solution following exposure to the stress inducing condition.

2. The method of claim 1, wherein the physiological solution is a physiological salt solution.

3. The method of claim 1, wherein the culture medium includes whole blood or a blood fraction.

4. The method of claim 3, wherein the blood fraction is serum.

5. The method of claim 1, wherein the PBMCs are cultivated following said stress inducing conditions for a period of at least 4 h.

6. The method of claim 5, wherein said period is at least 6 h.

7. The method of claim 6, wherein said period is at least 12 h.

8. The method of claim 1, wherein said topical pharmaceutical preparation is provided as a gel, ointment, dermal patch, cream, powder, liniment, or lotion.

9. The method of claim 8, wherein said topical pharmaceutical preparation is a dermal patch comprising a pharmaceutically acceptable matrix.

10. The method of claim 9, wherein said pharmaceutically acceptable matrix comprises a collagen/elastin matrix.

11. The method of claim 1, wherein the culture supernatant is lyophilized.

12. The method of claim 1, wherein said ischemia associated skin condition is selected from the group consisting of wounds, chronic wounds, diabetic wounds, skin ulcer, skin burns, skin flaps in plastic surgery, and tissue regeneration after dental grafting.

13. A method of topically treating an ischemia associated inflammatory skin condition by a step of administering a topical pharmaceutical preparation comprising a culture supernatant including components from a secretome produced in vitro by peripheral blood mononuclear cells (PBMCs) comprising T cells, B cells, NK cells, and monocytes separated from whole blood by Ficoll density gradient centrifugation, wherein the culture supernatant including components from the secretome is obtained by in vitro cultivation of the PBMCs for at least 1 h within a physiological solution that is a culture medium free of phytohemagglutinin (PHA) and lipopolysaccharide (LPS), wherein before or during the course of cultivation, the PBMCs are subjected to a stress inducing condition that includes irradiation with at least 60 Gy.

14. A method of topically treating an ischemia associated inflammatory skin condition by a step of administering a topical pharmaceutical preparation comprising a culture supernatant produced in vitro by non-proliferating peripheral blood mononuclear cells (PBMCs) comprising T cells, B cells, NK cells, and monocytes obtained by Ficoll density gradient centrifugation, wherein the culture supernatant includes a non cell-surface moiety triggered secretome production triggered by in vitro cultivation of the non-proliferating PBMCs for at least 1 h in a physiological solution free of phytohemagglutinin (PHA) and lipopolysaccharide (LPS), wherein before or during the course of cultivation, the PBMCs are subjected to irradiation with at least 60 Gy.

15. The method of claim 14, wherein the secretome in the topical pharmaceutical preparation consists essentially of the secretome produced by a combination of irradiated, non-proliferating and non-activated T cells, B cells, NK cells, and monocytes.

* * * * *